United States Patent
Honda et al.

(10) Patent No.: US 9,023,029 B2
(45) Date of Patent: *May 5, 2015

(54) TREATMENT SYSTEM

(71) Applicant: Olympus Medical Systems Corp., Tokyo (JP)

(72) Inventors: Yoshitaka Honda, Tokyo (JP); Takashi Irisawa, Tokyo (JP); Sadayoshi Takami, Tokyo (JP); Toshifumi Katsuragi, Tokyo (JP); Kazue Tanaka, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,224

(22) Filed: Jan. 23, 2014

(65) Prior Publication Data

US 2014/0236140 A1  Aug. 21, 2014

Related U.S. Application Data

(63) Continuation of application No. PCT/JP2013/065942, filed on Jun. 10, 2013.

(60) Provisional application No. 61/660,364, filed on Jun. 15, 2012.

(51) Int. Cl.
*A61B 18/12* (2006.01)
*A61B 18/04* (2006.01)
(Continued)

(52) U.S. Cl.
CPC ............. *A61B 18/1233* (2013.01); *A61B 18/04* (2013.01); *A61B 18/1445* (2013.01); *A61B 2018/00642* (2013.01); *A61B 2018/00898* (2013.01)

(58) Field of Classification Search
CPC ............. A61B 18/085; A61B 18/1233; A61B 18/1442; A61B 2018/00642; A61B 2018/00666; A61B 2018/00714; A61B 2018/00892; A61B 2018/00898
USPC ........... 606/27–29, 31, 34, 38, 41, 42, 51, 52; 607/99, 101
See application file for complete search history.

(56) References Cited

U.S. PATENT DOCUMENTS 4,744,359 A   5/1988  Hatta et al.
6,740,085 B2 *  5/2004  Hareyama et al. ............. 606/51
(Continued)

FOREIGN PATENT DOCUMENTS

JP   B2-01-034618   7/1989
JP   A-11-197158    7/1999
(Continued)

OTHER PUBLICATIONS

Aug. 20, 2013 International Search Report issued in International Patent Application No. PCT/JP2013/065942 (with English translation).

*Primary Examiner* — Michael Peffley
*Assistant Examiner* — Thomas Giuliani
(74) *Attorney, Agent, or Firm* — Oliff PLC (57) ABSTRACT

A treatment system includes a holding section that has a heat generation section, a signal output section that supplies a drive signal to the heat generation section, a setting section that sets a target temperature of the heat generation section, a signal detection section that detects the drive signal, a signal extraction section that extracts an extracted signal of a predetermined frequency band from the drive signal detected by the signal detection section, a fault detection section that detects a precursory phenomenon of a fault of the heat generation section when the extracted signal reaches a predetermined threshold, and a control section that controls the drive signal to the heat generation section in a treatment mode for treating the living tissue at the target temperature or in a test mode for detecting the precursory phenomenon.

6 Claims, 11 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 2006/0069388 A1* | 3/2006 | Truckai et al. | 606/45 |
| 2009/0088740 A1* | 4/2009 | Guerra et al. | 606/41 |
| 2009/0157075 A1* | 6/2009 | Wham et al. | 606/40 |
| 2011/0037484 A1* | 2/2011 | Gilbert | 324/649 |
| 2013/0150848 A1 | 6/2013 | Yasunaga | |
| 2014/0207132 A1* | 7/2014 | Honda et al. | 606/31 |
| 2014/0214142 A1* | 7/2014 | Honda et al. | 607/112 |

FOREIGN PATENT DOCUMENTS

| | | |
|---|---|---|
| JP | A-2006-288430 | 10/2006 |
| JP | B2-3911334 | 2/2007 |
| JP | A-2012-070779 | 4/2012 |
| WO | WO 2012/043469 A1 | 4/2012 |

* cited by examiner

TREATMENT SYSTEM

CROSS REFERENCE TO RELATED APPLICATION

This application is a continuation application of PCT/JP2013/065942 filed on Jun. 10, 2013 and claims benefit of U.S. Provisional Patent Application No. 61/660,364 filed in the U.S.A. on Jun. 15, 2012, the entire contents of which are incorporated herein by this reference.

BACKGROUND OF THE INVENTION

1. Field of the Invention

The present invention relates to a treatment system that treats a living tissue held between a pair of holding sections by applying thermal energy thereto.

2. Description of the Related Art

Treatment systems are known which apply thermal energy to a living tissue held between a pair of holding sections of a treatment instrument. Such treatment systems coagulate or dissect a living tissue to be treated such as blood vessel.

Japanese Patent Application Laid-Open Publication No. 2012-70779 discloses a treatment system in which a pair of holding sections have a heat generation section and the heat generation section has a structure with a plurality of heat generating substrate portions including a thin film resistors connected via conductors. In this treatment system, the holding sections have a high degree of temperature uniformity and the holding sections can be easily downsized.

Here, although the treatment system is designed/manufactured so as to fully satisfy high-level reliability, faults are unavoidable. However, even when a fault occurs, if the fault position can be immediately identified, the treatment can be continued by replacing the faulty part by a spare part. For example, in the case where a fault is attributable to wire breakage or the like of the heat generation section of the treatment instrument of the treatment system, the faulty treatment instrument may be replaced by a spare treatment instrument.

Japanese Patent No. 3911334 and Japanese Patent Publication No. 01-34618 disclose a treatment system that monitors resistance or the like of a heat generation section, judges a fault when the resistance falls outside a predetermined range and notifies a user of the fault.

SUMMARY OF THE INVENTION

A treatment system according to an embodiment includes a holding section that has a heat generation section for applying thermal energy and holds a living tissue, a signal output section that supplies a drive signal to the heat generation section, a setting section that sets a target temperature of the heat generation section, a signal detection section that detects the drive signal pressure, a signal extraction section that extracts an extracted signal of a predetermined frequency band from the drive signal detected by the signal detection section as an extracted signal, a fault detection section that detects a precursory phenomenon of a fault of the heat generation section when the extracted signal reaches or exceeds a predetermined threshold, and a control section that controls the drive signal supplied from the signal output section to the heat generation section in either one of a treatment mode for treating the living tissue at the target temperature or of a test mode for detecting the precursory phenomenon.

DETAILED DESCRIPTION OF THE PREFERRED EMBODIMENTS

First Embodiment

Hereinafter, a treatment system 1 according to a first embodiment of the present invention will be described with reference to the accompanying drawings.

Figure 1:
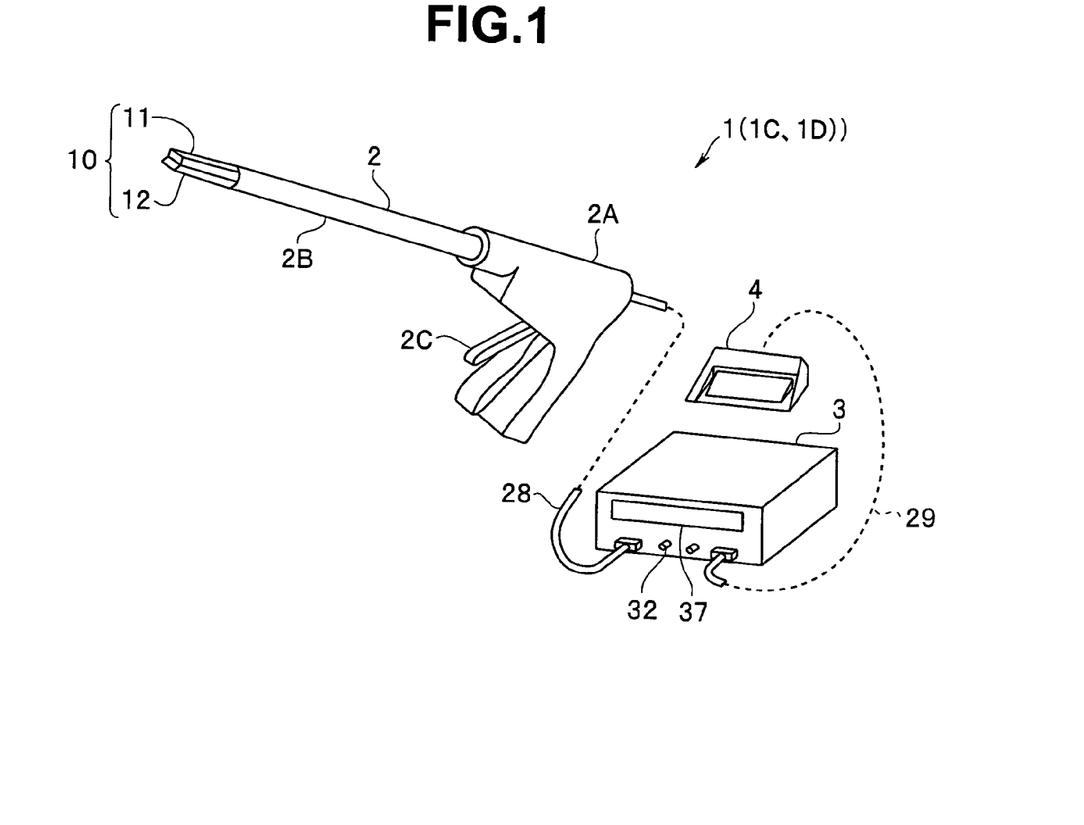
FIG. 1 is a perspective view illustrating an overall configuration of a treatment system according to a first embodiment.

As shown in FIG. 1, the treatment system 1 is provided with a treatment instrument 2, a main unit 3 and a foot switch 4. The treatment instrument 2 is a linear type instrument for surgery that performs treatment, for example, through an abdominal wall.

The treatment instrument 2 is provided with a grip 2A, a shaft 2B, and a pair of openable/closable holding sections 10 (a first holding section 11 and a second holding section 12) that hold and treat a living tissue LT to be treated. The grip 2A is connected to the main unit 3 via a cable 28. The grip 2A provided with an opening/closing knob 2C whereby an operator opens/closes the holding sections 10 has an easy-to grip shape, for example, an approximately L shape. The shaft 2B is disposed at an end of the grip 2A, which is integrated with the holding sections 10 to transmit operation of the opening/closing knob 2C to the holding sections 10. On the other hand, the other end of the grip 2A is a grasping portion grasped by the operator.

The main unit 3 has, on its front panel, a display section 37 that displays treatment conditions or the like and a setting section 32 for the operator to set the treatment conditions or the like, and the foot switch 4 is connected thereto via a cable 29. When the operator presses a pedal of the foot switch 4 with his/her foot, ON/OFF of a drive signal from the main unit 3 to the treatment instrument 2 is controlled. Note that the foot switch 4 is not an essential component, and the foot switch may be substituted by a switch or the like operated by the operator on his/her hand side.

Figure 2A:
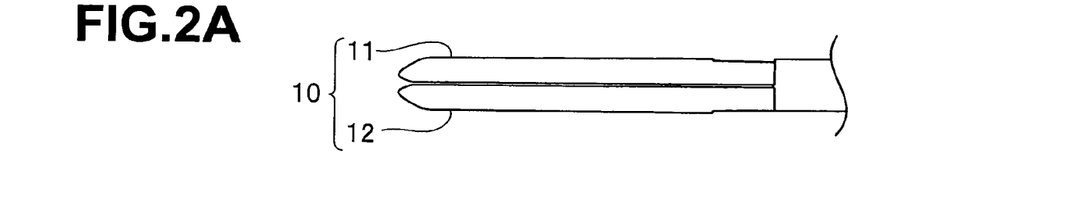
FIG. 2A is a side view of a pair of holding sections (closed state) of the treatment system of the first embodiment.
Figure 2B:
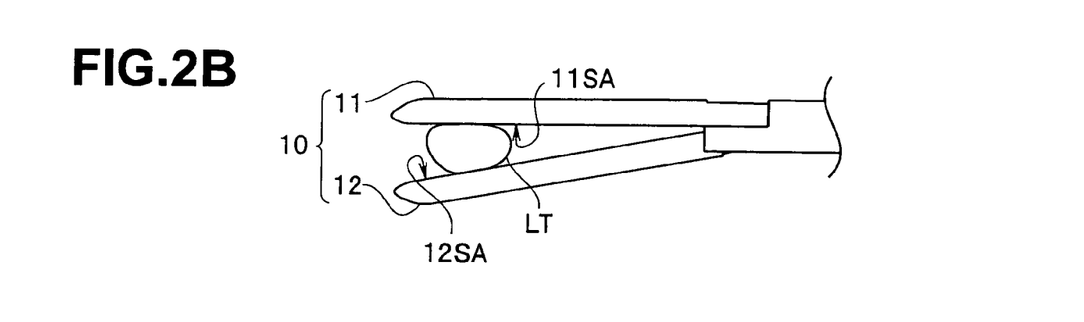
FIG. 2B is a side view of the treatment system of the first embodiment when the pair of holding sections hold a living tissue.

As shown in FIG. 2A and FIG. 2B, the holding section 10 can be freely opened/closed when the second holding section 12 moves relative to the first holding section 11. That is, as shown in FIG. 2A, when the opening/closing knob 2C is not pressed by the operator, the second holding section 12 is proximate to or in contact with the first holding section 11 by an urging force of an elastic member (not shown). On the other hand, when the opening/closing knob 2C is pressed by the operator with a force stronger than the urging force of the elastic member as shown in FIG. 2B, the second holding section 12 detaches from the first holding section 11 and the holding section 10 is left open. While the holding section 10 is open, if the operator stops the operation of the opening/closing knob 2C, the living tissue LT inserted between the first holding section 11 and the second holding section 12 is held by being sandwiched and pressed between a holding surface 11SA of the first holding section 11 and a holding surface 12SA of the second holding section 12 by the urging force of the elastic member.

Figures 3A, 3B, 3C:
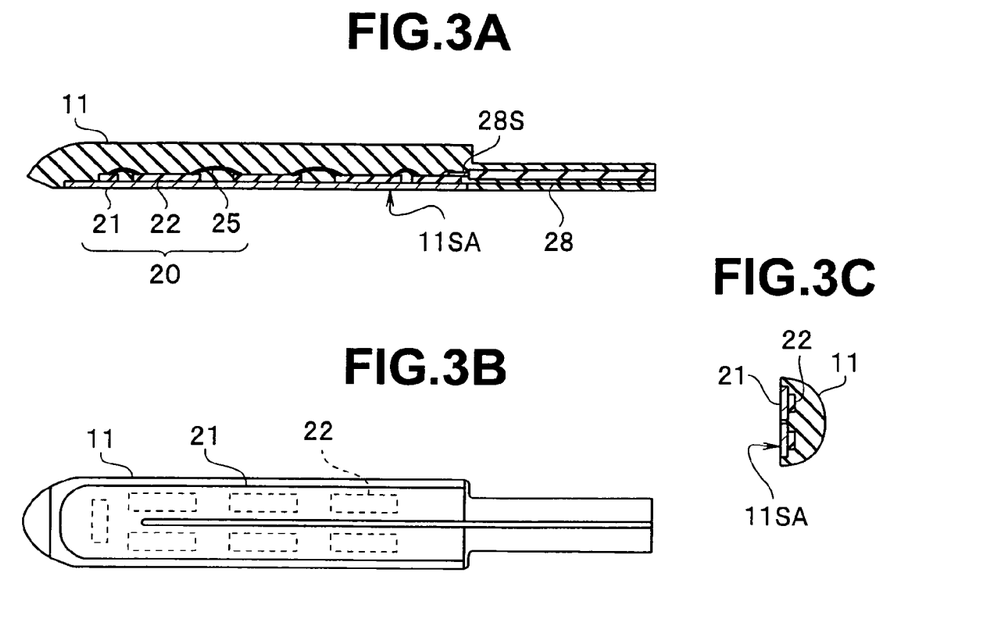
FIG. 3A is a diagram illustrating a cross-sectional structure in a major axis direction of a first holding section of the treatment system of the first embodiment.
FIG. 3B is a top view of the first holding section of the treatment system of the first embodiment.
FIG. 3C is a diagram illustrating a cross-sectional structure in a minor axis direction of the first holding section of the treatment system of the first embodiment.
Figure 4:
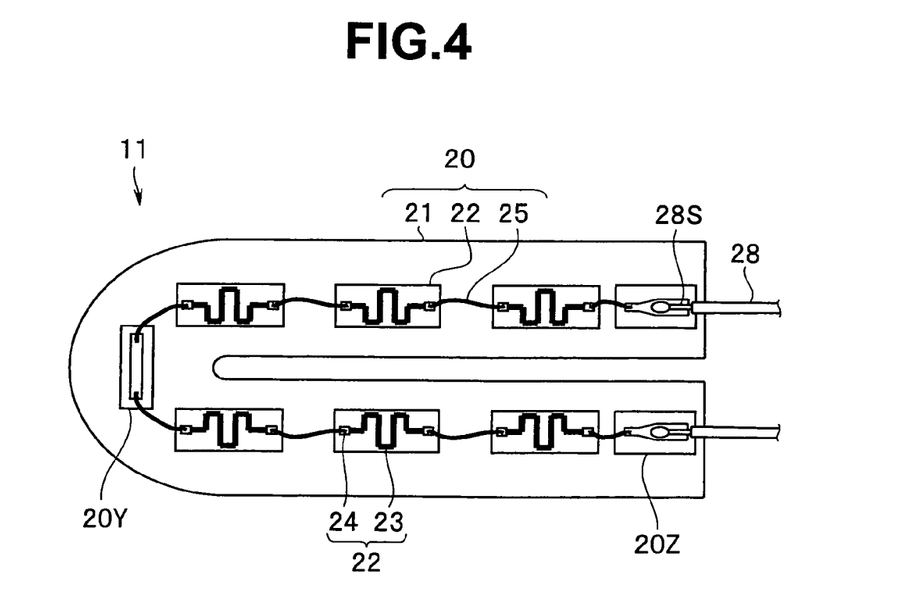
FIG. 4 is a top view illustrating a heat generation section of the first holding section of the treatment system of the first embodiment.

As shown in FIG. 3A to FIG. 4, a heat generation section 20 that generates thermal energy is disposed on the holding surface 11SA of the first holding section 11. The heat generation section 20 is made up of a plurality of heat generating substrate portions 22 bonded to the back side (inner surface side) of a metal electrode substrate 21 which is, for example, a copper or SUS thin plate.

The heat generating substrate portion 22 is made of an insulator such as alumina or nitride aluminum, on a front side of which a thin film resistor 23 made of a metal such as platinum is formed. Platinum is a material having a positive temperature coefficient of resistance whose electric resistance R increases as its temperature rises. For this reason, it is possible to measure a temperature of the heat generation section 20 (thin film resistor 23) from the resistance R of the thin film resistor 23 as will be described later. The material of the thin film resistor 23 is not limited to platinum, and a high melting point metal material with various kinds of positive temperature coefficient of resistance such as NiCr alloy, Ta or W may also be used.

An electrode pad 24 made up of a multilayer film of, for example, Ti/Cu/Ni/Au is formed at an end of the thin film resistor 23. The thin film resistors 23 of the plurality of heat generating substrate portions 22 are connected in series via conductors 25 that connect the electrode pads 24 using, for example, a wire bonding technique. Note that as shown in FIG. 4, a relay substrate portion 20Y may be disposed between the plurality of heat generating substrate portions 22. A connection substrate portion 20Z is disposed at the farthest end of the plurality of heat generating substrate portions 22 connected in series and a conductor 28S of a cable 28 is connected to the connection substrate portion 20Z.

Note that the plurality of heat generating substrate portions 22 of the heat generation section 20 may also be, for example, partially connected in parallel. Moreover, each heat generating substrate portion 22 may have a plurality of thin film resistors 23. Note that a heat generation section similar to that of the first holding section 11 may also be disposed on the second holding section 12 and the two heat generation sections may be connected in series or in parallel.

A metal film (not shown) is formed on a main surface (back side) opposing a surface of the heat generating substrate portion 22 on which the thin film resistor is formed, and bonded to the metal electrode substrate 21 via, for example, a brazing metal having high thermal conductivity. For this reason, heat generated from the thin film resistor 23 is efficiently transferred to the metal electrode substrate 21 (holding surface 11SA).

Note that the surface of the first holding section 11 on which the thin film resistor is formed (front surface) is covered with an insulator such as polyimide and insulated. In order to prevent any adverse effect on living tissues surrounding the living tissue to be treated, the outer surface of the holding section 10 may be preferably made of a material having low thermal conductivity.

Figure 5:
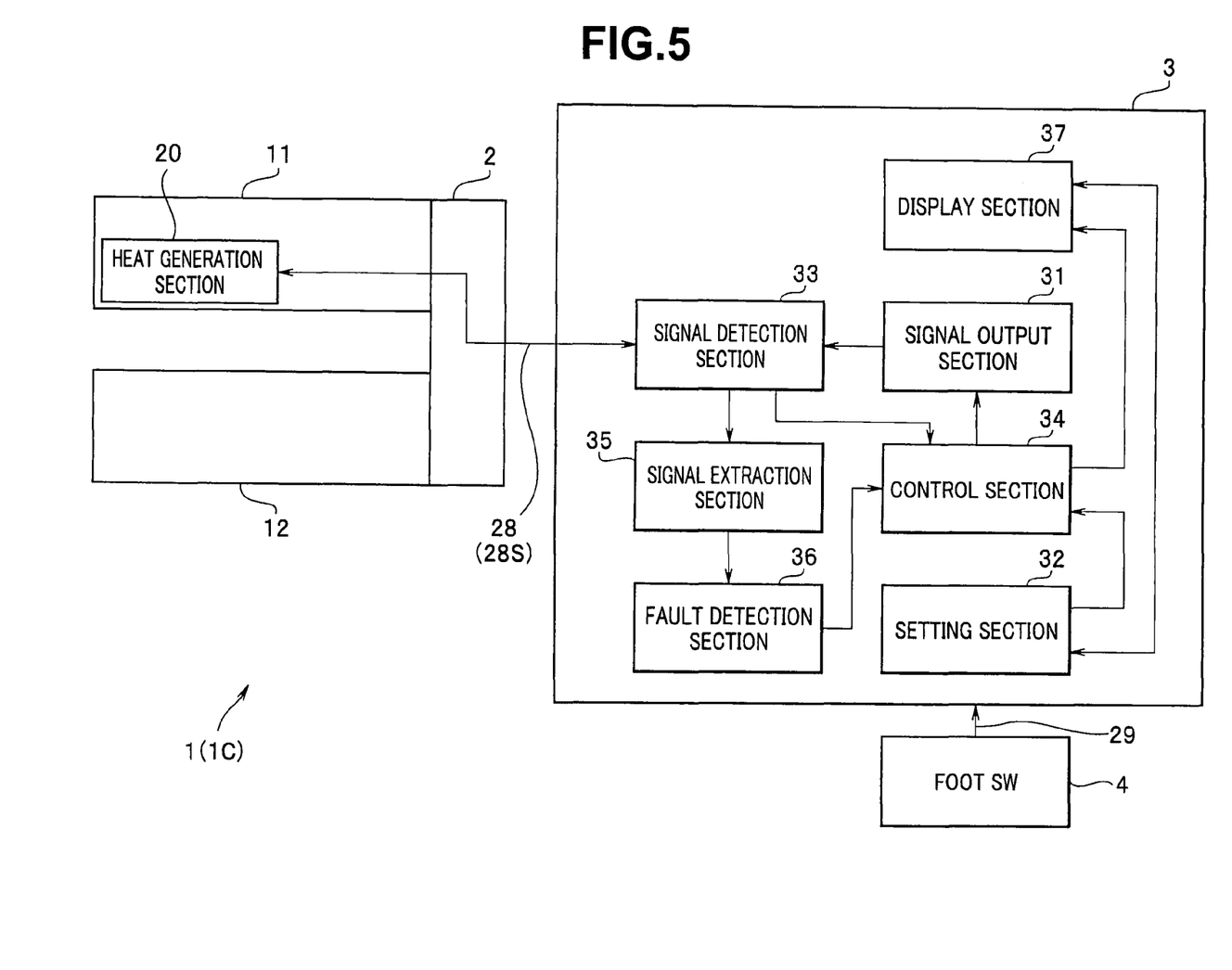
FIG. 5 is a configuration diagram of the treatment system of the first embodiment.

Next, the configuration of the treatment system 1 will be described using FIG. 5. As has already been described, the treatment system 1 has the treatment instrument 2, the main unit 3 and the foot switch 4.

The main unit 3 has a signal output section 31, a setting section 32, a signal detection section 33, a control section 34, a signal extraction section 35, a fault detection section 36, and a display section 37.

The signal output section 31 is made up of, for example, a high frequency signal oscillation section and an amplifier for supplying a drive signal, that is, heat generating power to the heat generation section 20. The setting section 32 is a switch, a mouse or a keyboard or the like used by the operator to set a target temperature T-set or the like of the heat generation section 20. The signal detection section 33 is a current sensor and a voltage sensor that detect a current I and a voltage V of a drive signal. Note that the signal detection section 33 may also be included in the treatment instrument 2. Moreover, to secure electrical safety, when the drive signal outputted from the signal output section 31 is an alternating current signal, the drive signal is transmitted to the treatment instrument 2 via, for example, a pulse transformer. The control section 34 is a CPU or the like that controls temperature of the heat generation section 20 by adjusting power ($W=I \times V$) of the drive signal. The signal extraction section 35 is a filter circuit that extracts a signal of a predetermined frequency band from the drive signal detected by the signal detection section 33. The fault detection section 36 detects a precursory phenomenon of a fault of the heat generation section 20 based on the extracted signal extracted from the signal extraction section 35.

Note that since the signal output section 31 and the signal detection section 33 process an analog signal, and the control section 34 processes a digital signal, the main unit 3 is provided with an AD conversion section (not shown).

As has already been described, the display section 37 displays a temperature of the heat generation section 20 during treatment, displays a temperature when the operator sets the target temperature T-set using the setting section 32, and also has a function of an announcement section that announces a warning as will be described later.

Note that the main unit 3 may have a high frequency signal output section. A high frequency signal outputted from the high frequency signal output section is applied to the pair of metal electrode substrates 21 of the treatment instrument 2. The operator can perform treatment on the living tissue LT held between the pair of holding sections 20 using high frequency energy in addition to thermal energy. The signal output section having the function of the high frequency signal output section and the function of the signal output section 31 may alternately generate a high frequency signal and a drive signal for heat generation.

Next, operation of the treatment system 1 will be described with reference to the flowchart in FIG. 6.

<Step S11> Setting of Target Value

The operator sets a target temperature T-set of the heat generation section 20 which is a target value for treatment using the setting section 32. The target temperature T-set varies depending on the living tissue LT to be treated and may be, for example, 100° C. to 300° C. Note that at this time, a treatment end time t-end or the like may also be set. The treatment end time t-end is a treatment time period after the temperature becomes the target temperature T-set, for example. Note that the treatment end time t-end may be automatically set in accordance with an impedance or the like of the living tissue LT.

<Step S12> Holding of Living Tissue

As shown in FIG. 2A, the holding section 10 is in a closed state and is inserted, for example, into the abdominal cavity through the abdominal wall. When the operator performs pressing operation by grasping the opening/closing knob 2C of the grip 2A, the second holding section 12 is opened relative to the first holding section 11. The living tissue LT to be treated is then placed between the holding surface 11SA of the first holding section 11 and the holding surface 12SA of the second holding section 12. When the opening/closing knob 2C is released in this condition, the second holding section 12 is closed relative to the first holding section 11 by an urging force of the elastic member and the living tissue LT to be treated is held, pressed between the holding surface 11SA of the first holding section 11 and the holding surface 12SA of the second holding section 12.

<Step S13> Output of Drive Signal

While the living tissue LT is held between the pair of holding sections 10, the operator presses the foot switch 4 with his/her foot. The control section 34 then controls the signal output section 31 so as to output a drive signal. The drive signal is transmitted to the heat generation section 20 of the treatment instrument 2 via the cable 28. That is, the drive signal is applied to the thin film resistor 23 via the conductor 28S of the cable 28, the connection substrate portion 20Z of the heat generation section 20 and the conductor 25, and the thin film resistor 23 generates heat. The heat generated by the thin film resistor 23 is transferred to the living tissue LT via the heat generating substrate portion 22 and the metal electrode substrate 21.

<Step S14> Detection of Drive Signal

The signal detection section 33 detects a current I and a voltage V of the drive signal. As has already been described, since the thin film resistor 23 is made of a material having a positive temperature coefficient of resistance, when the temperature rises, the electric resistance R increases in proportion thereto. For this reason, it is possible to acquire the temperature of the heat generation section 20 by calculating the resistance R from the current I and the voltage V of the drive signal and using a prestored relationship expression between resistance and temperature. Of course, a temperature sensor may also be disposed in the heat generation section 20. However, it is possible to acquire the temperature of the heat generation section 20 in a simple configuration using the thin film resistor 23 made of a material having a positive temperature coefficient of resistance.

Figure 7:
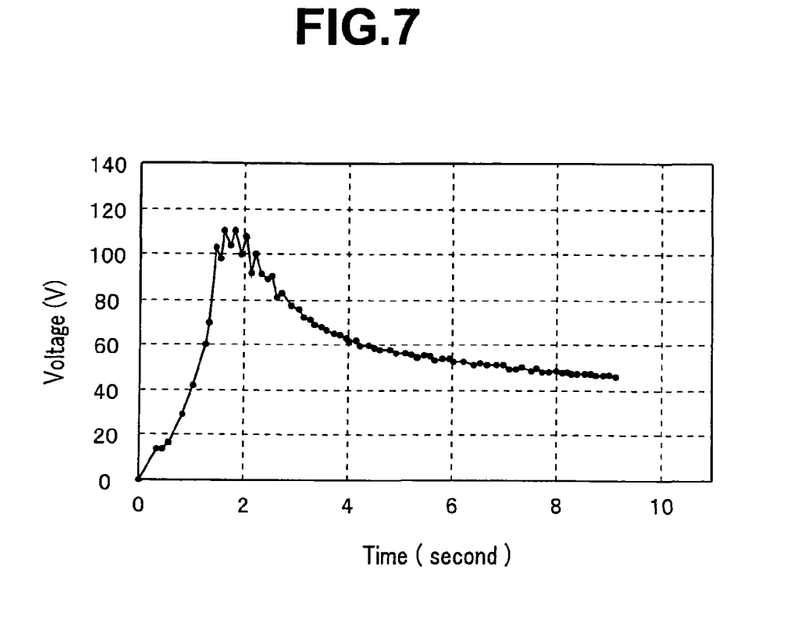
FIG. 7 is a diagram illustrating a drive signal of the treatment system of the first embodiment during normal operation.

The control section 34 controls the signal output section 31 so that the temperature of the heat generation section 20 becomes the target temperature T-set and thereby adjusts power W of the drive signal, that is, the current I and the voltage V. For this reason, as shown in FIG. 7, during normal operation, the drive signal (voltage) monotonously increases and then monotonously decreases with time. This is because while large power is required to heat the living tissue LT from the body temperature to the target temperature T-set, only small power is enough to maintain the living tissue LT at the target temperature T-set.

Figure 8:
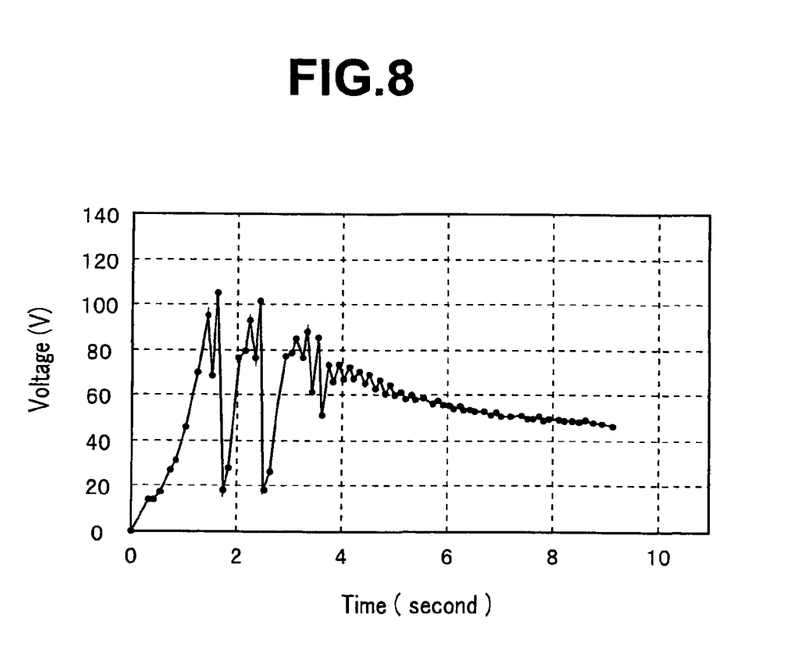
FIG. 8 is a diagram illustrating a drive signal of the treatment system of the first embodiment when a precursory phenomenon has occurred.

In contrast, the present inventor discovered that the drive signal may specifically change as shown in FIG. 8. Note that the treatment system 1 can perform normal treatment even when the drive signal changes as shown in FIG. 8. However, after the drive signal changes, drastically increasing/decreasing for a short period as shown in FIG. 8, if the treatment system 1 is continued to be used, the heat generation section 20 often malfunctions. For this reason, the occurrence of the drive signal change shown in FIG. 8 is called a "precursory phenomenon" of a fault.

It is unknown why this precursory phenomenon occurs. However, when treatment was performed several to over ten times after the precursory phenomenon occurred, the probability that wire breakage would occur, causing a fault of the heat generation section 20 of the treatment instrument 2 was high.

<Step S15> Signal Extraction

In the treatment system 1, the signal extraction section 35 extracts a signal (extracted signal) of a predetermined frequency band from the drive signal detected by the signal detection section 33. That is, the signal extraction section 35 is a band pass filter function section that allows a signal of a predetermined frequency band to pass and does not allow signals of other frequency bands to pass therethrough. For example, the signal extraction section 35 is made up of a high pass filter and a low pass filter. The low pass filter is intended to smooth a signal and facilitate conversion to a digital signal that can be processed by the CPU which is the control section 34, and the high pass filter is intended to extract only a change that increases or decreases for a short period of time.

The signal detection section 33 detects the current I and the voltage V of the drive signal, whereas the extraction target of the signal extraction section 35 may be either the current I or the voltage V. The extraction target may also be power (W) or resistance (R) calculated from the current I and the voltage V.

The range of the frequency band extracted by the signal extraction section 35 is selected as appropriate in accordance with characteristics of the treatment system 1, and in order to distinguish the change of a drive signal (voltage) during normal operation shown in FIG. 7 from the change of a drive signal (voltage) which is the precursory phenomenon shown in FIG. 8, for example, the range of the frequency band extracted preferably has a lower limit of, for example, 0.1 Hz or above and an upper limit of 20 Hz or below, and more preferably a lower limit of 1 Hz or above and an upper limit of 10 Hz or below.

When the range of the frequency band is equal to or greater than the above-described range, it is possible to detect a change during normal operation and a change in the event of a precursory phenomenon by distinguishing one from the other, and no problem occurs at the time of AD conversion processing if the range falls within the above-described range.

Note that although the detailed structure is different from the heat generation section 20 of the treatment system 1, in a treatment system having a heat generation section in which a thin film resistor is also connected via a conductor, it is possible to detect a precursory phenomenon of a fault (wire breakage) of the heat generation section 20 by extracting a drive signal having the same frequency band as that of the treatment system 1. Thus, it has been confirmed that the precursory phenomenon is a common phenomenon among wire breakage faults in a heat generation section of a treatment system having the heat generation section in which thin film resistors are connected via a conductor.

Figure 9:
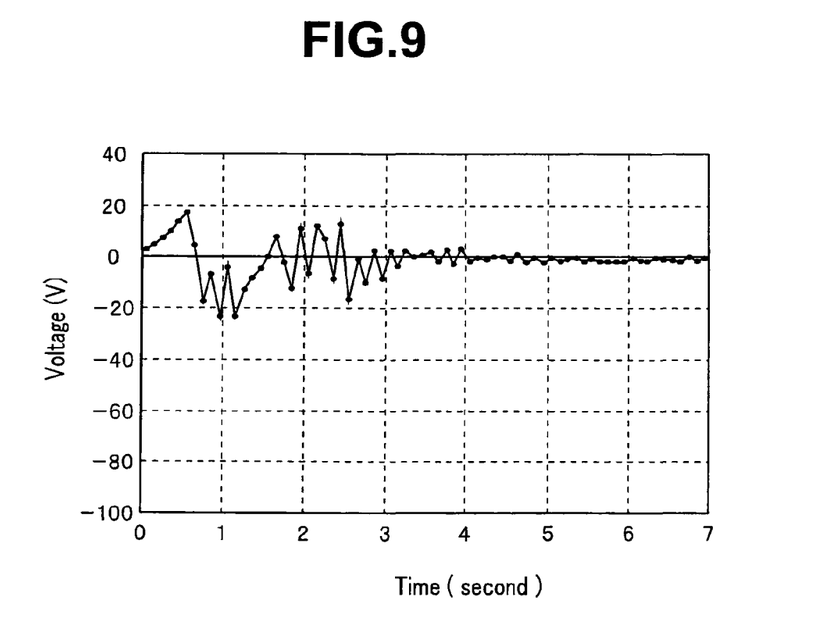
FIG. 9 is a diagram illustrating an extracted signal of the treatment system of the first embodiment during normal operation.
Figure 10:
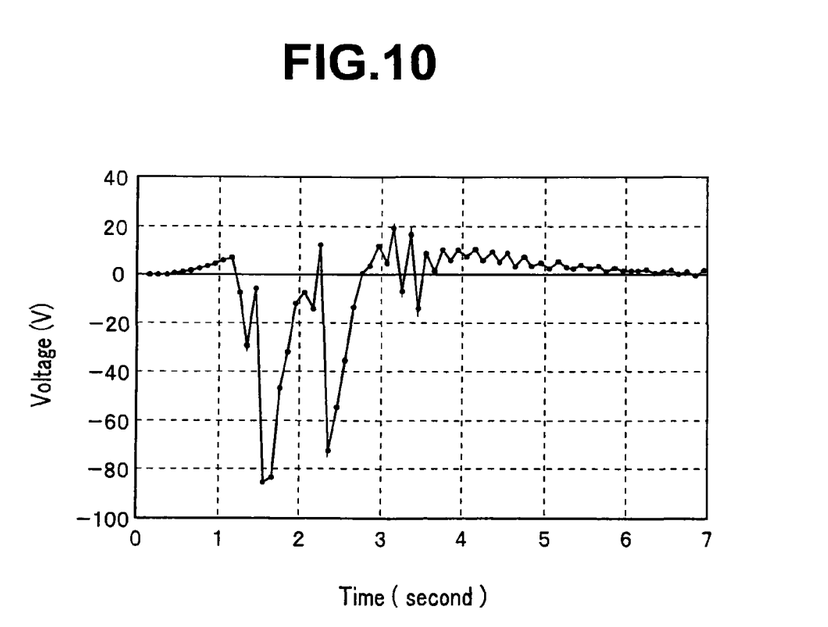
FIG. 10 is a diagram illustrating an extracted signal of the treatment system of the first embodiment when a precursory phenomenon has occurred.

FIG. 9 illustrates an extracted signal (voltage) during normal operation from which the signal extraction section 35 has extracted a signal of a frequency band of (1 Hz to 10 Hz) from the drive signal (voltage) during normal operation shown in FIG. 7 and FIG. 10 illustrates an extracted signal (voltage) from the drive signal (voltage) shown in FIG. 8 in which the precursory phenomenon has occurred.

<Step S16> Detection of Precursory Phenomenon

The fault detection section 36 detects a precursory phenomenon of a fault of the heat generation section 20 based on an extracted signal extracted by the signal extraction section 35. For example, when a maximum value of an absolute value of the extracted signal is equal to or above a predetermined threshold (S16: Yes), the fault detection section 36 assumes it as a precursory phenomenon of a fault of the heat generation section 20. For example, in the case shown in FIG. 8, the threshold voltage is set to on the order of 40 V.

For example, the fault detection section 36 is made up of a reference voltage generation section that generates a predetermined threshold voltage and a comparator that compares the threshold voltage with the extracted signal, and outputs the comparison result to the control section 34 using, for example, a digital signal.

In order to detect a precursory phenomenon, the fault detection section 36 may also use an integral value of the extracted signal or a differential value of the extracted signal instead of a maximum value of the extracted signal.

<Step S17> Announcement of Warning

When the fault detection section 36 detects a precursory phenomenon (S16: Yes), the control section 34 controls the display section 37 which is an announcement section to display a warning. For the announcement of a warning, speech using a speaker (not shown) or the like may be used or an LED (not shown) or the like may be lit yellow. A warning may be announced after completing one treatment so as to prevent any confusion of the operator.

Note that the fault detection section 36 may not only detect a precursory phenomenon but also detect a fault of the heat generation section 20 from a drive signal. When a fault, that is, wire breakage occurs in the heat generation section 20, the electric resistance R increases significantly, and so it is easy to detect the fault. When the fault detection section 36 detects a fault, the control section 34 controls the display section 37 which is an announcement section so as to display a warning and also controls it so as to stop outputting a drive signal from the signal output section 31. Note that a warning may be announced by lighting an LED (not shown) or the like red.

<Step S18> Setting Change

Note that a time period from the occurrence of a precursory phenomenon to the occurrence of a fault may be very short. In this case, even if a precursory phenomenon is detected, a fault may occur before the treatment is completed and the treatment cannot be completed. For this reason, when the fault detection section 36 detects a precursory phenomenon (S16: YES), the control section 34 may perform control so as to reduce at least one of the target temperature T-set and power W of the drive signal.

For example, reducing the target temperature T-set extends the time period until the occurrence of a fault (wire breakage), and therefore the treatment can be completed. Note that when the target temperature T-set or power W is reduced, the treatment end time t-end may be preferably automatically extended so that predetermined thermal energy may be applied to the living tissue LT to be treated.

Note that step S18 is not an essential step for the treatment system 1.

<Step S19> (Treatment Mode)

When the fault detection section 36 does not detect any precursory phenomenon (S16: No), the control section 34 performs normal control. That is, the control section 34 performs steps from step S13 until the treatment end time t-end elapses (S19: Yes), that is, the control section 34 controls the signal output section 31 so that the temperature of the heat generation section 20 becomes the target temperature T-set and adjusts power of the drive signal.

When the treatment end time t-end elapses (S19: Yes), the holding section 10 is extracted from within the abdominal cavity. Of course, when no precursory phenomenon is detected and the treatment is continued, the treatment from S11 or S12 is repeatedly done.

As described above, in the treatment system 1, the signal extraction section 35 extracts a signal of a predetermined frequency band from the drive signal detected by the signal detection section 33 and the fault detection section 36 detects a precursory phenomenon of a fault of the heat generation section 20 based on the extracted signal. Thus, since the treatment instrument can be replaced by a spare treatment instrument after the treatment is completed, it is possible to prevent a fault from occurring while the treatment is in progress. When the setting change function is provided, it is possible to prevent a fault from occurring while the treatment is in progress by extending the time period until a fault occurs.

Therefore, the treatment system 1 can speedily complete the treatment.

Second Embodiment

Next, a treatment system 1C according to a second embodiment will be described. Since the treatment system 1C is similar to the treatment system 1, the same components are assigned the same reference numerals and description thereof will be omitted.

In the treatment system 1C, the control section 34 performs control in either one of control modes: a treatment mode for treating a living tissue LT and a test mode for reliably detecting a precursory phenomenon. The test mode is executed without the holding section 10 holding any living tissue LT.

As has already been described, even when the fault detection section 36 detects a precursory phenomenon of a fault during a treatment, the treatment can be accomplished in many cases. The treatment instrument can be replaced by a spare treatment instrument before starting the next treatment.

However, there is no denying a possibility that the fault detection section 36 may mistakenly detect a precursory phenomenon. For example, due to a faulty connection between the cable 28 and the main unit 3, results similar to a precursory phenomenon may be obtained. The test mode is a mode for confirming whether a precursory phenomenon detected by the fault detection section 36 is correct or not.

Figure 11:
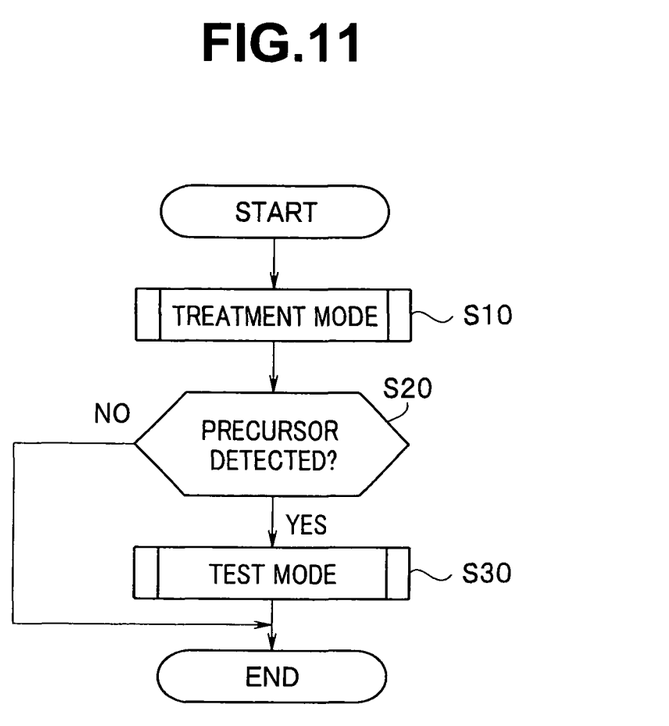
FIG. 11 is a flowchart illustrating a treatment flow of a treatment system according to a second embodiment.
Figure 12:
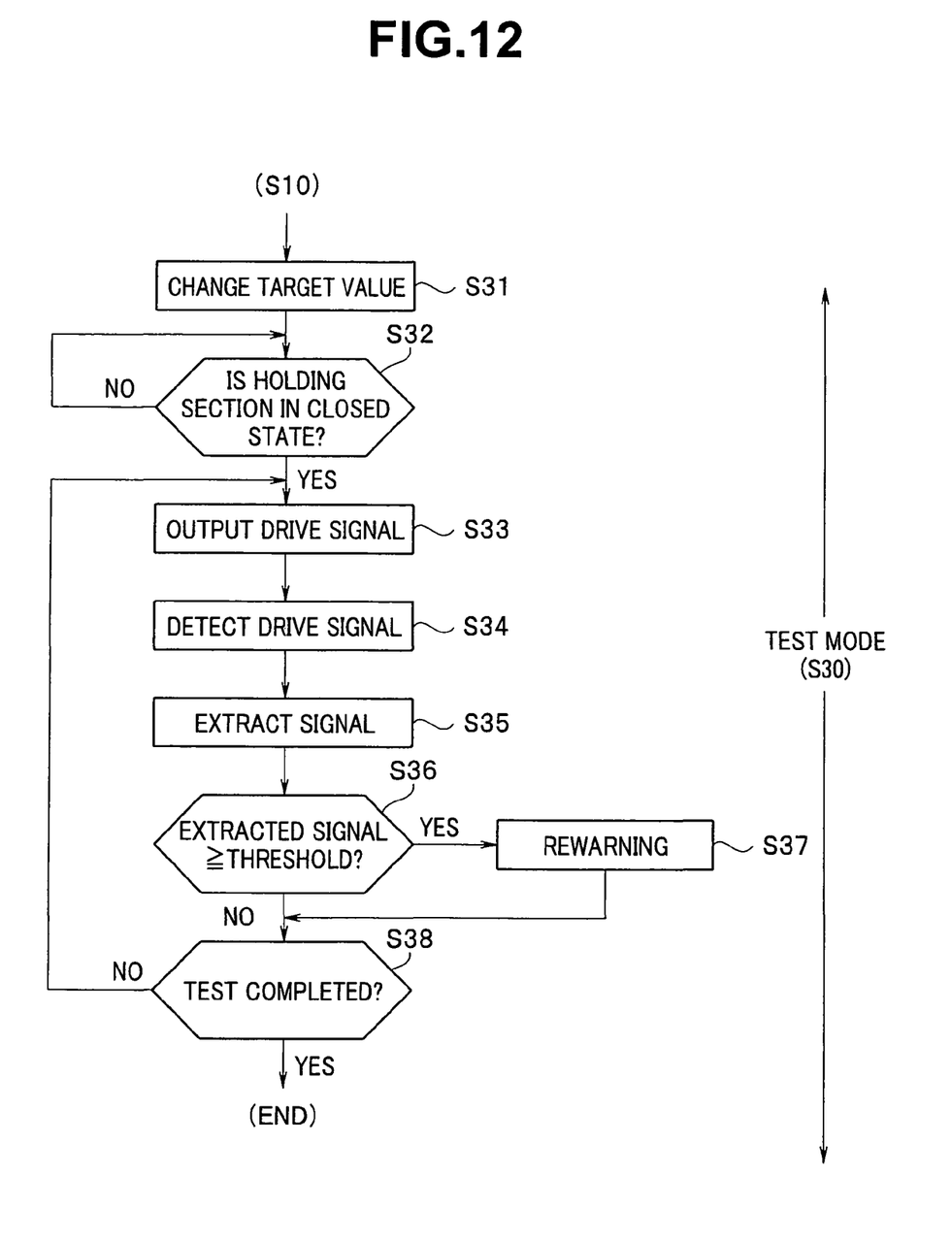
FIG. 12 is a flowchart illustrating test mode processing.

Hereinafter, operation of the treatment system 1C will be described according to flowcharts in FIG. 11 and FIG. 12.

<Step S10> Treatment Mode Subroutine

Figure 6:
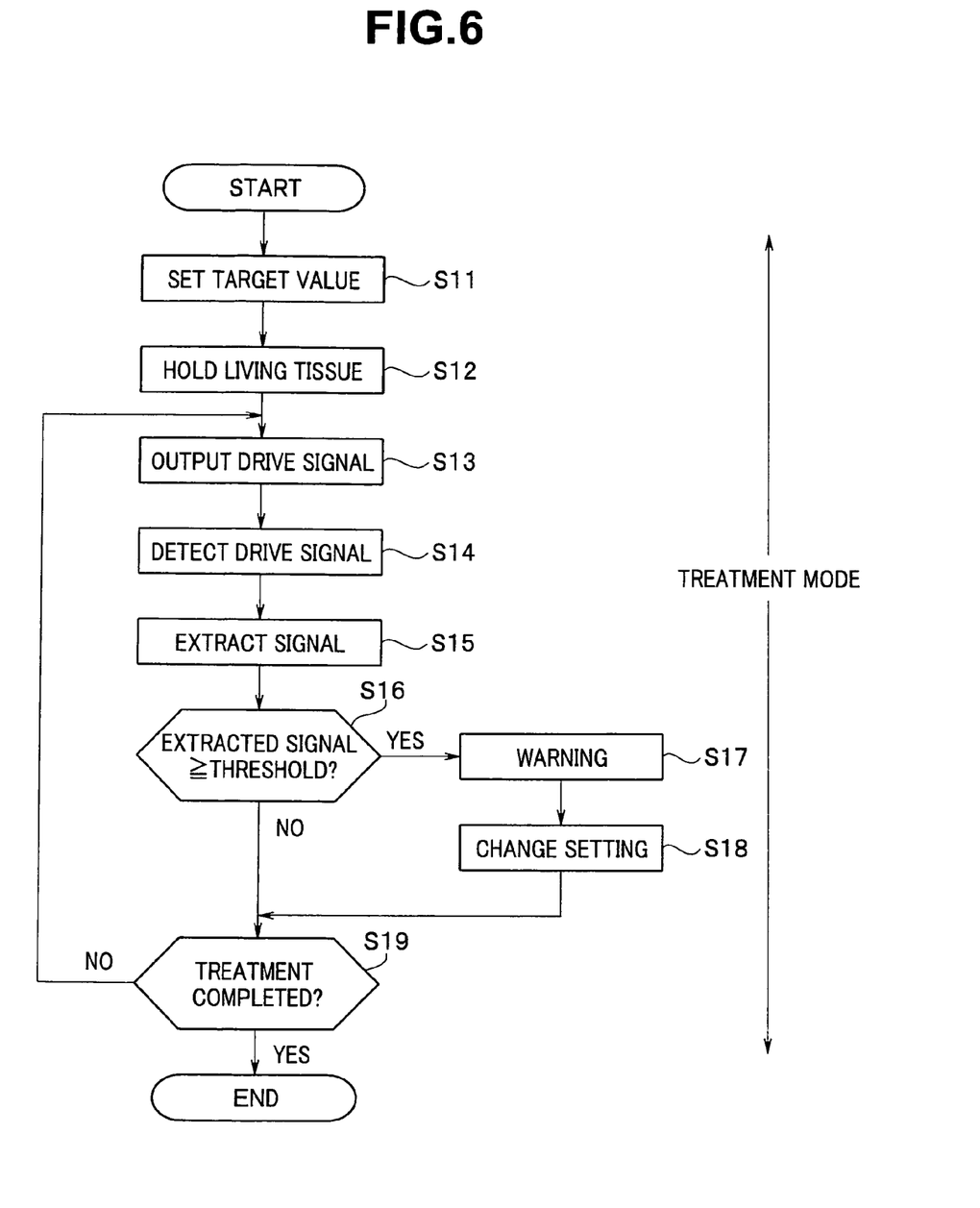
FIG. 6 is a flowchart illustrating a treatment flow of the treatment system of the first embodiment.

Since the treatment mode subroutine is the same as steps S11 to S19 of the treatment system 1 already described using FIG. 6, description thereof will be omitted.

<Step S20>

When a treatment is completed, if a precursory phenomenon is detected during the treatment, that is, during treatment mode processing (S20: Yes), the control mode of the treatment system 1C is changed from the treatment mode to the test mode and S30 (test mode subroutine) is executed. Since a treatment in the test mode is shifted after completion of the treatment, the treatment is done outside the subject. When no precursory phenomenon is detected (S20: No), the treatment is completed.

Note that a mode shift may be selected by the operator instead of an automatic mode shift.

<Step S30> Test Mode Subroutine

<Step S31>

The control section 34 performs control in the test mode by increasing a target value set in the treatment mode, for example, at least one of the target temperature T-set and the power W of the drive signal. That is, the test mode is a high load test (acceleration test) in which a wire breakage fault is more likely to occur in the heat generation section 20 than in the normal treatment mode.

For example, the target temperature T-set may be increased by 10% or power W of the drive signal, that is, at least one of the current I and the voltage V may be increased by 10%. Note that the order of step S31 and following step S32 may be reversed.

<Step S32>

The test mode is preferably done when the holding section 10 is in a closed state. The heated heat generation section 20 being exposed to the outside is not only dangerous, but since the heat generated by the heat generation section 20 is likely to be dissipated and the temperature is less likely to rise in an open state, excessive power may be applied to the heat generation section 20 as a consequence and cause damage to the normal heat generation section.

Figure 13:
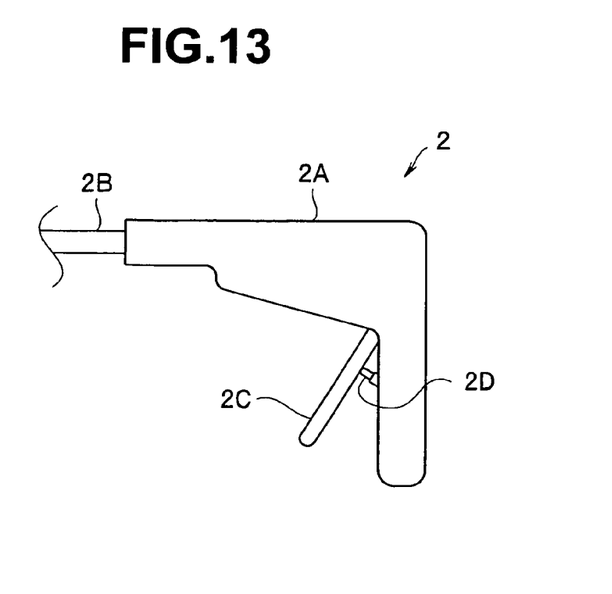
FIG. 13 is a side view of the treatment instrument of the treatment system of the embodiment.

In the treatment system 1C, the holding section 10 may be preferably in a closed state, in other words, the treatment system 1C may be preferably provided with an open/closed state detection section 2D that detects an open/closed state of the holding section 10. For example, as shown in FIG. 13, in the treatment system 1C, the open/closed state detection section 2D is disposed in the grip 2A and is a sensor that detects whether the opening/closing knob 2C is pressed or not. As the sensor, for example, a mechanical sensor, an optical sensor or a magnetic sensor may be used.

The detection result of the open/closed state detection section 2D is transmitted to the control section 34 and the control section 34 stands by until the holding section 10 is set in a closed state (S32: YES). Note that when the open/closed state detection section 2D detects that the holding section 10 is set in an open state during the test, the test may be stopped.

Figure 14:
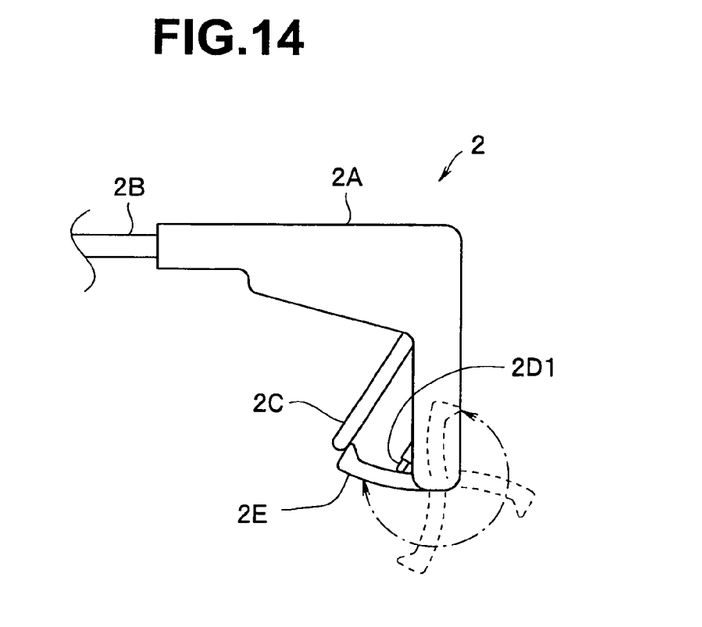
FIG. 14 is a side view of the treatment instrument of the treatment system of the embodiment.

As shown in FIG. 14, to prevent the holding section 10 from being mistakenly set in an open state, for example, a ratchet 2E that rotates relative to the opening/closing knob 2C may be disposed and an open/closed state detection section 2D1 may detect the state of the ratchet 2E. Note that when not used, the ratchet 2E is accommodated in the opening/closing knob 2C.

When the ratchet 2E is engaged, even if the operator mistakenly presses the opening/closing knob 2C during a test, no force is transmitted to the holding section 10, and therefore the holding surface 11SA and the holding surface 12SA are kept being pressed by a constant urging force of the elastic member. For this reason, in the treatment system 1C provided with the ratchet 2E, the temperature of the heat generation section 20 rises particularly stably.

Figure 15:
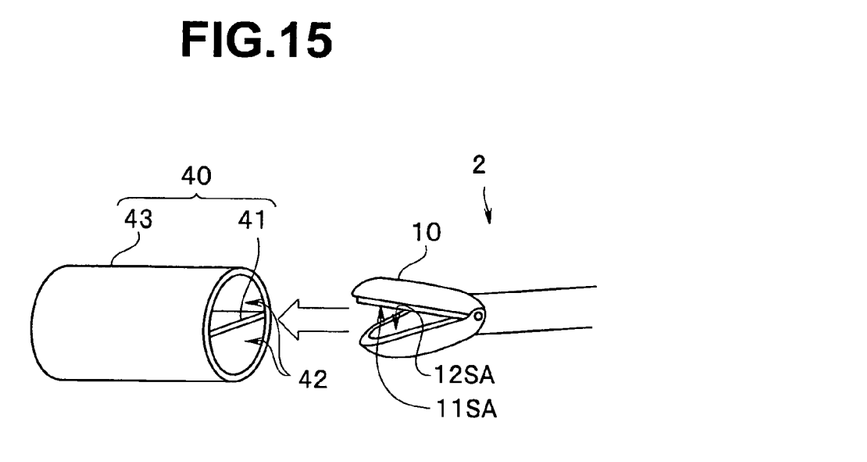
FIG. 15 is a perspective view illustrating a holding section holder of the treatment system of the embodiment.
Figure 16A:
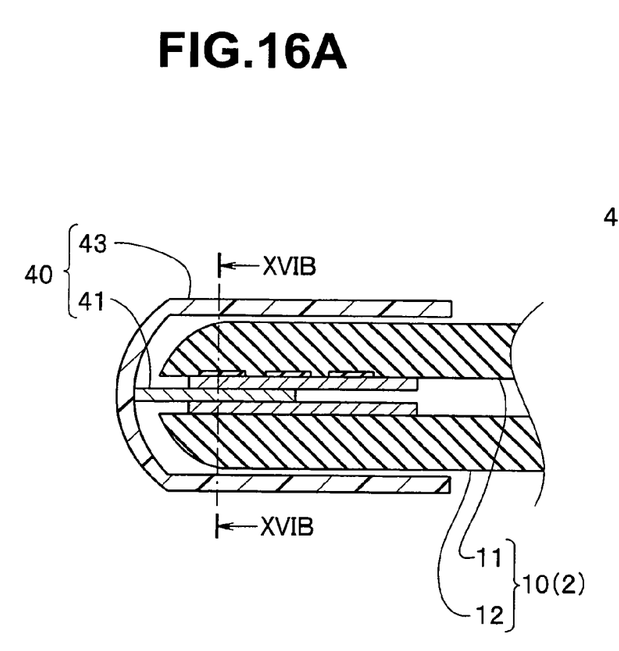
FIG. 16A is a cross-sectional view of the holding section holder in which the holding section of the treatment system of the embodiment is accommodated.
Figure 16B:
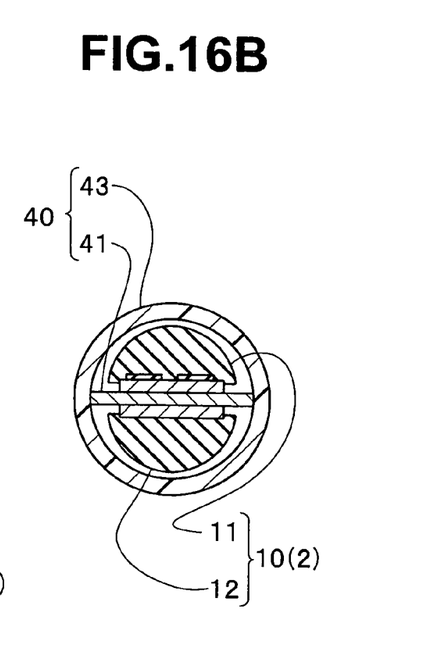
FIG. 16B is a cross-sectional view along a line XVIB-XVIB of FIG. 16A.

Furthermore, as shown in FIG. 15, FIG. 16(A) and FIG. 16(B), the treatment system 1 preferably includes a holding section holder 40. The holding section holder 40 is constructed of a protective member 43 made of a high heat insulating material which has a cavity portion 42 that can accommodate the holding section 10 that generates heat. As the high heat insulating material, heat-resistant resin or the like is used. Heat generated by the holding section 10 is not transferred to the outer surface of the holding section holder 40. It is thereby possible to prevent accidents caused by contact with the holding section 10 heated outside the body. Of course, the holding section 10 may be accommodated in the holding section holder 40 also for storage in other than the test mode for prevention of damage or the like to the holding section 10.

The holding section holder 40 is also provided with a conductive member 41 held between the holding surface 11SA and the holding surface 12SA. Even for a treatment instrument provided with a holding section in which the holding surface 11SA and the holding surface 12SA are designed not to be pressed even in a closed state according to its specification or the like, the holding surface 11SA and the holding surface 12SA are pressed via the conductive member 41 having high thermal conductivity.

Note that an elastic body may be used to constitute the protective member 43 and the holding section 10 may be pushed into the cavity portion 42 which is slightly smaller than the external size of the holding section 10 so that the holding surface 11SA and the holding surface 12SA may be kept pressed.

<Step S33> Drive Signal Output

When the holding section 10 is in a closed state (S32: Yes), if the operator presses the foot switch 4 by his/her foot, the signal output section 31 outputs a drive signal in a test mode under the control of the control section 34.

<Steps S34 to S36>

These are substantially the same as steps S14 to S16 in the treatment mode already described using FIG. 6.

<Steps S37 and S38>

When the fault detection section 36 detects a precursory phenomenon (S36: Yes), the control section 34 controls the display section 37 which is the announcement section so as to display a warning again. On the contrary, when the fault detection section 36 does not detect any precursory phenomenon (S36: No), for example, an LED (not shown) or the like may be lit green after completion of the test (S38: Yes).

That is, the LED is lit green during normal operation, yellow when a precursory phenomenon is detected and red in the event of a fault.

The treatment system 1C of the second embodiment has the effects of the treatment system 1, and in addition, can more reliably detect a precursory phenomenon of a fault.

Modification of Second Embodiment

Next, a treatment system 1D according to a modification of the second embodiment will be described. Since the treatment system 1D is similar to the treatment system 1C, the same components are assigned the same reference numerals and description thereof will be omitted.

Figure 17:
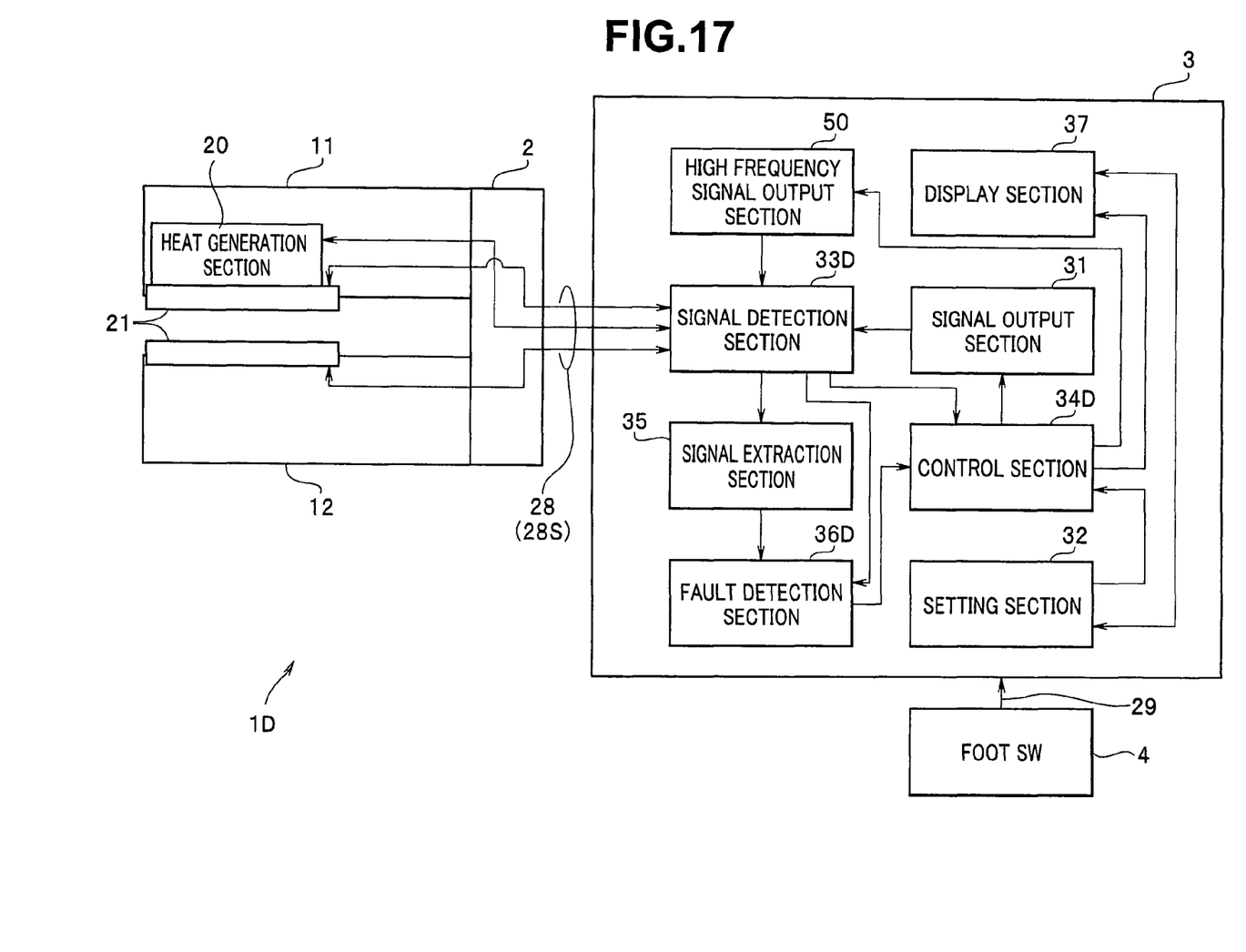
FIG. 17 is a configuration diagram of a treatment system according to a modification of the second embodiment.

As shown in FIG. 17, the treatment system 1D is provided with a high frequency signal output section 50 that outputs a high frequency signal to be applied between the holding surfaces. For example, a high frequency signal made up of a sine wave of 350 kHz is applied to the pair of metal electrode substrates 21 of the treatment instrument 2. The living tissue LT held pressed between the pair of metal electrode substrates 21 is a conductor containing a large percentage of water content. Thus, high frequency energy is applied to the living tissue LT as Joule heat derived from the resistance of the living tissue LT, Joule heat derived from contact resistance between the living tissue LT and the metal electrode substrate 21, or heat and shock wave or the like derived from a discharge phenomenon between the metal electrode substrate 21 and the living tissue LT.

The operator can perform treatment on the living tissue LT held between the holding sections 10 using high frequency energy in addition to thermal energy.

In the treatment system 1D, a fault detection section 36D detects an open/closed state of the holding section 10 based on an impedance (resistance) of the high frequency current detected by a signal detection section 33D. That is, if the resistance when a high frequency current is applied to the pair of metal electrode substrates 21 is higher than a predetermined threshold resistance, the fault detection section 36D detects that the holding section 10 is in an open state.

The treatment system 1D has the effects of the treatment system 1C and further has a simple structure since the fault detection section 36D has a function of an open/closed state detection section. Of course, the signal detection section 33D may be constructed of a heat generation signal detection section and a high frequency current detection section, or may have an open/closed state detection section different from the fault detection section 36D. The treatment system 1D may also be provided with the open/closed state detection section 2D or 2D1 shown in FIG. 13 and FIG. 14, and may determine that the control section is in a closed state only when both the detection result of the fault detection section 36D and the detection result of the open/closed state detection section 2D or the like are in a closed state.

Note that in the holding section holder 40 used in the treatment system 1D, the conductive member 41 is preferably not disposed in the vicinity of the opening of the cavity portion 42. This is intended to detect that the heat generation section 20 of the holding section 10 is completely accommodated in the cavity portion 42.

The present invention is not limited to the above-described embodiments, but various changes, alterations or the like may be made without departing from the spirit and scope of the present invention.

What is claimed is:

1. A treatment system comprising:
a holding section that has a heat generation section for applying thermal energy and is configured to hold a living tissue;
a signal output section configured to supply a drive signal to the heat generation section;
a setting section configured to set a target temperature of the heat generation section;
a signal detection section configured to detect the drive signal;
a signal extraction section configured to extract an extracted signal of a frequency band within a range of 0.1 Hz to 20 Hz from the drive signal detected by the signal detection section;
a fault detection section configured to detect a precursory phenomenon of a fault of the heat generation section when the extracted signal reaches or exceeds a predetermined threshold;
a control section configured to control the target temperature of the heat generation section by adjusting power of the drive signal; and
an announcement section configured to announce a warning, when the fault detection section has detected the precursory phenomenon.

2. The treatment system according to claim 1, wherein the heat generation section comprises a heat generating substrate portion having a thin film resistor, the heat generating substrate portion being connected to a conductor.

3. The treatment system according to claim 1, wherein, when the fault detection section has detected the precursory phenomenon, the control section controls the signal output section so as to decrease the drive signal.

4. The treatment system according to claim 1, wherein, when the fault detection section has detected the precursory phenomenon, the control section decreases the target temperature set by the setting section and controls the signal output section so as to decrease the drive signal.

5. The treatment system according to claim 1, wherein the fault detection section comprises:
a threshold signal generation section configured to generate the predetermined threshold; and
a comparator configured to compare the extracted signal with the predetermined threshold.

6. The treatment system according to claim 5, wherein the predetermined threshold is a threshold voltage.

* * * * *